United States Patent [19]

Holzner

[11] Patent Number: 4,475,906
[45] Date of Patent: Oct. 9, 1984

[54] PARTIALLY FLEXIBLE INJECTION SYRINGE DEVICE WITH PRESSURE RELEASE VALVE OR SPECIAL BREAKABLE SEAL

[76] Inventor: Günter Holzner, Rue Montfalcon, 8, CH - 1227 Carouge, Switzerland

[21] Appl. No.: 417,628

[22] Filed: Sep. 13, 1982

[51] Int. Cl.³ ............................................. A61M 5/00
[52] U.S. Cl. ..................................... 604/212; 604/187
[58] Field of Search ................. 604/212, 187, 181, 93; 128/760, 766, 767

[56] References Cited

U.S. PATENT DOCUMENTS

| | | | |
|---|---|---|---|
| 2,862,496 | 12/1958 | Hassler et al. | 604/212 |
| 3,114,369 | 12/1963 | Hall | 604/212 |
| 3,128,920 | 4/1964 | Volckening et al. | 604/212 |
| 3,424,148 | 1/1969 | Cadeillan | 604/212 |
| 3,736,933 | 6/1973 | Szabo | 604/212 |
| 3,933,439 | 1/1976 | McDonald | 128/767 |

*Primary Examiner*—John D. Yasko
*Attorney, Agent, or Firm*—Scully, Scott, Murphy & Presser

[57] ABSTRACT

New injection syringe devices are formed of a partially flexible plastic bag which is filled with the solution to be injected. On one end there is a hollow injection needle sealed in. To separate the solution from the needle and to make the injection device tight during storage, a pressure release valve or special breakable seal is used.

When a certain mechanical pressure is exerted on the outer side of the plastic bag the overpressure valve opens automatically or the breakable seal ruptures. With both systems it is possible to make ready-to-use prefilled injection devices consisting of a closed flexible plastic bag with the needle on one end. Pressure on the outside of the bag by hand or a mechanical device opens the junction between the plastic bag and the needle thus permitting the liquid content to be injected. An elastic plastic bulb inserted between needle and flexible plastic bag which is compressed by finger pressure immediately before injection thus permitting the withdrawal of blood when released to identify venous or arterial penetration.

The aim of the invention is the mass production of a cheap, sterilized and ready-to-use injection device. This injection packaging contains the injection liquid prefilled and sterilized and the injection needle already fixed. It is not necessary as with conventional injection technique to store the injection liquid in a glass ampoule and to suck it in the injection syringe prior to use.

18 Claims, 8 Drawing Figures

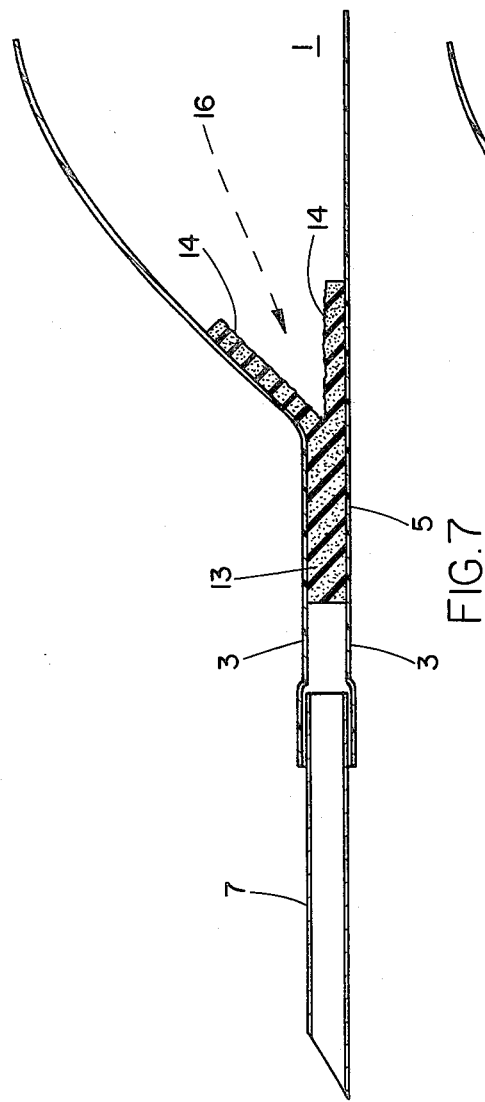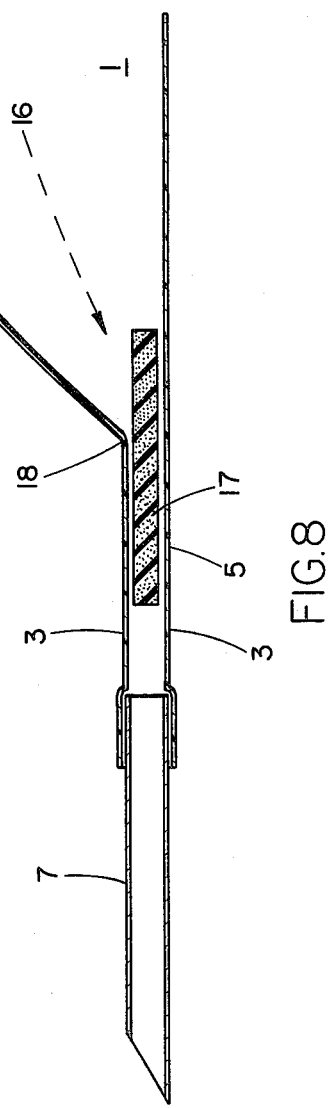

4,475,906

PARTIALLY FLEXIBLE INJECTION SYRINGE DEVICE WITH PRESSURE RELEASE VALVE OR SPECIAL BREAKABLE SEAL

BACKGROUND OF THE INVENTION

The actual single use injection syringes are of the classical piston-pump type. The injection liquid has to be stored separately in an ampoule. Immediately before use the ampoule is opened and the injection liquid is sucked in. In many cases the needle and the injection syringe are packed separately and have to be assembled prior to use. This handling needs some experience and when not correctly done contamination of needle and liquid is possible.

The injection device described in this invention does not need any assembling or filling prior to use. It is easy to produce and to use.

The U.S. Pat. No. 3,736,933 (June 5, 1973) describes already a similar injection packaging formed from flexible plastic tubing with a hollow needle sealed therein. To hinder the flowing out of liquid during storage a breakable normally heat sealed seam of decreasing thickness is positioned between the filled plastic tube and the needle. By finger pressure imposed on the outer walls of the tube the seal bursts and opens the way to the needle. Practical tests revealed that it is very difficult in production to make the seal in a manner that it ruptures correctly without external leakage. Due to the the flexibility over the whole body of the device it is difficult to squeeze it out completely by finger pressure. This hypodermic applicator does not permit aspiration of blood samples which is important for intravenous injections and to take small diagnostic blood samples as will be described later.

The U.S. Pat. No. 2,744,527 (May 8, 1956) describing a syringe-ampoule system where the needle penetrates a membrane prior to injection, or the two parts of a rigid multicompartmented device are separated by a flexible tube closed by a screw, does not interfere with our patent claim.

The U.S. Pat. No. 3,757,981 (Sept. 11, 1973) describes a valve needle syringe system where the valve has to be opened by hand prior to injection.

Finally the U.S. Pat. No. 4,130,117 (Dec. 19, 1978) describes a deformable ampoule with needle where a rupturable membrane extends across the neck portion sealing a medicament in the ampoule. This membrane has an outside tab to break it prior to use. Our patent claims may be distinguished from the forementioned patents because the opening of our flexible injection device is made in both cases (using the pressure release valve or breakable seam) by simple pressure on the outside of the device.

SUMMARY OF THE INVENTION

An object of our invention is a partially flexible plastic container (sachet or bag) filled with the injection liquid where the separation of liquid and needle is achieved by a pressure release valve or by a special multilayer seal. Both devices permit an easy and correct opening of the plastic bag and the injection of the liquid when mechanical pressure on the outer wall of the bag is exterted. The plastic bag is only partially flexible. It has two rigid side walls where the pressure by finger or mechanical device is exterted. This construction permits to squeeze out completely the content of the bag.

A self-expanding bag can be made of an elastic plastic material. The empty bag is compressed before inserting the needle in a vein or other body cavity. On expansion, the bag aspirates a corresponding volume of liquid.

BRIEF SUMMARY OF THE DRAWINGS

FIG. 7—Schematic drawing of the breakable foam layer.

FIG. 8—Schematic drawing of the breakable seam with Surlyn ®.

DETAILED DESCRIPTION OF THE PREFERRED EMBODIMENTS

Figure 1:
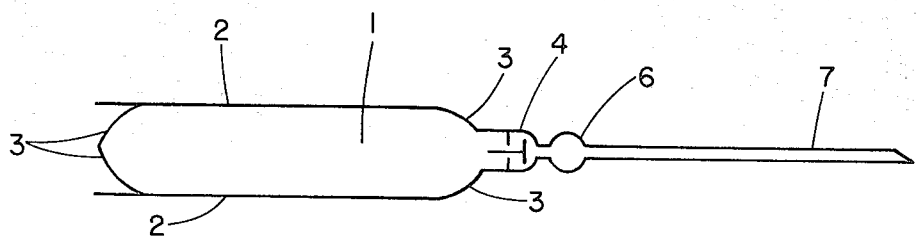
FIG. 1—Schematic sideview of the injection device with pressure release valve.
Figure 2:
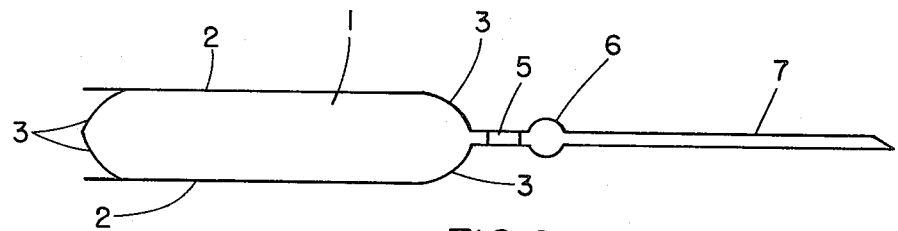
FIG. 2—Schematic sideview of the injection device with breakable seam.
Figure 3:
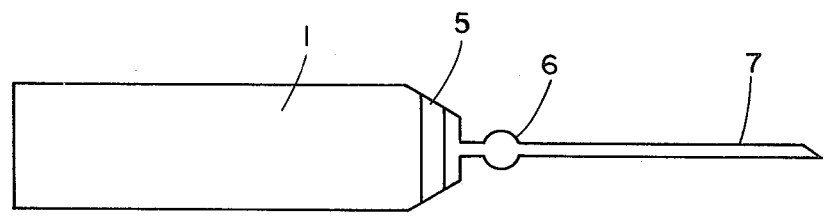
FIG. 3—Schematic plan view of the injection evice with breakable seam.
Figure 4:
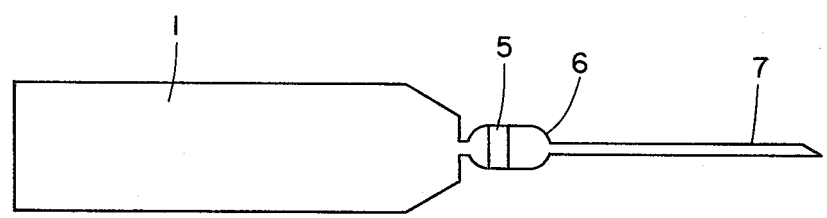
FIG. 4—Schematic plan view of the breakable seam in the elastic bulb.
Figure 5:
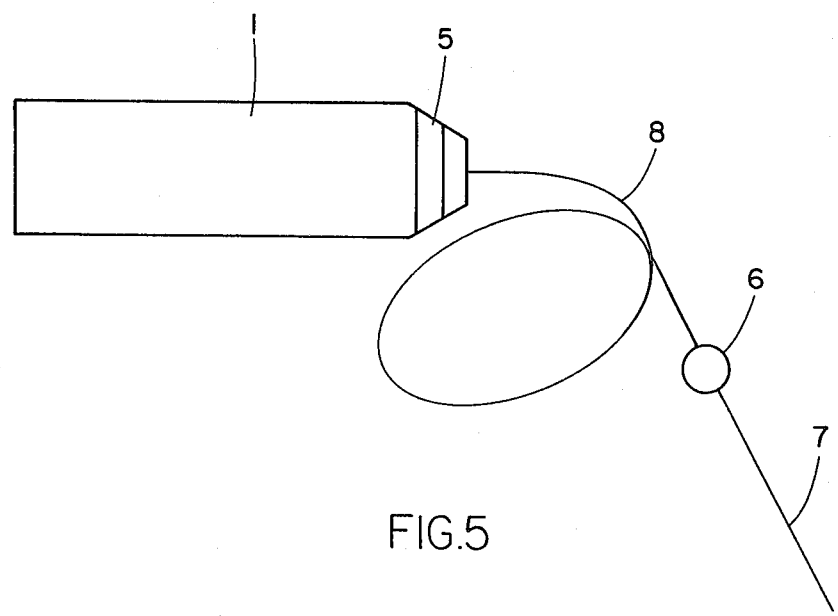
FIG. 5—Schematic plan view of the injection device with breakable seam and flexible tube.
Figure 6:
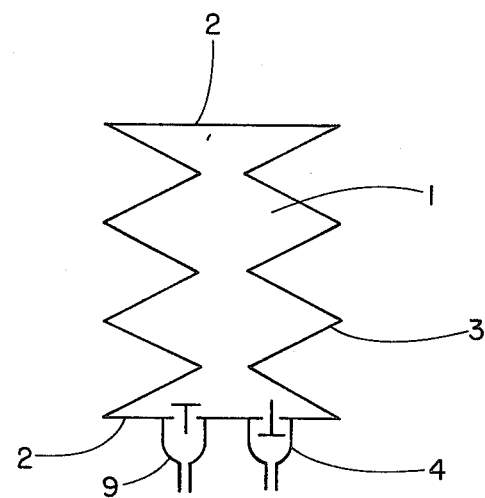
FIG. 6—Schematic view of multi-injection device.

As illustrated in FIGS. 1 to 4, in the production of this aforementioned injection device the injectable liquid is sealed in a flexible plastic bag 1 having rigid walls 2 annd flexible walls 3. This bag is connected by a small channel or tube to a hypodermic needle 7. The junction between sachet and needle is closed during storage by a pressure release valve 4 or a special multilayer seam 5.

As illusttrated in FIGS. 7 and 8, when starting the injection a pressure is applied by hand or a simple mechanical forceps device. The over-pressure 16 in the bag opens the valve or breaks the multi-layer seam 5 as illustrated at 14 in FIG. 7 or 18 in FIG. 8, and therefore permits the injection of the liquid by continuous pressure on the bag until it is completely emptied.

The closing of the aforementioned junction plastic bag-needle is obtained in two different ways:

(a) a small pressure release valve where a steel spring or an elastic rubber part exerts the closing force of the valve. The counterpressure of the liquid during injection opens automatically the valve. This system permits also the construction of a simple multiinjection pump: a concertina shaped elastic plastic bag contains two of these valves: one inlet valve which is in connection with a storage tank of the injection liquid and the pressure release valve in connection with the injection needle. Pressing down the plastic bag effects injection, release of the pressure permits a further dose of the injection liquid from the storage container to enter the bag.

(b) a multilayer seam 5 blocks the connection between the needle 7 and the plastic bag 1. Exceeding a certain pressure inside the injection liquid this seam breaks and opens the way to the needle. One type of this seam consists of a 3 layer sandwich foil where a thin foam foil 17 or foam layer 13 is sealed between two cover foils 13. When the plastic bag is put under pressure 16 the foam layer breaks in longitudinal direction that means it cleaves in two parts 14 opening the seam inside without damaging the cover foils illustrated in FIG. 7.

The advantages of this system are:
1. The cover foils 3 stay absolutely intact.
2. The force necessary for opening the seam can be regulated by the inner density of the foam layer 13

(coarse texture—easier rupturing). The foam layer 13 can be made from any plastic which can be rendered porous by foaming or other treatments e.g. polyethylene, polypropylene, copolymere of polyethylene and vinyl acetate or ethyl acrylate, polyamide, polyvinylchloride and polystyrene. For easier production the inside of the plastic sachet can be covered completely or partially with the described foam layer. Another possibility as illustrated in FIG. 8, to form a breakable seal 5 is to use Surlyn ® (Dupont), a polyethylene containing ionic groups, as a layer 17 between two polyethylene films 3. Surlyn ® forms a solid but breakable welding with polyethylene. By blending the Surlyn with 1–20% of a polyethylene-ethyl-acrylate or polyethylene-vinyl acetate copolymere resin the adhesion of Surlyn ® to polyethylene can be increased. This gives a method to regulate the pressure 16 necessary for breaking the seam indicated at 18 in FIG. 8. Another object of the present invention is an injection needle for the forementioned partially flexible injection device.

The previously described injection system and all similar systems based on flexible injection devices have the following disadvantage: for intravenous injection (conventional system) the needle is firstly introduced into the vein. To test if the point is correctly situated the operator withdraws the piston of the injection syringe a little. If some droplets of blood enter easily the syringe the needle is correctly inserted in the interior of the vein. This control is not possible with closed, flexible, prefilled injection devices. The following construction of the needle for prefilled flexible injection devices permits the foregoing described control: a small, transparent, elastic plastic bulb 6 is inserted between the outlet of the plastic bag 1 and the inlet of the hollow injection syringe 7. Immediately before puncturing the operator compresses the plastic bulb 6 keeping it under fingerpressure till the needle is correctly in the interior of the vein, then releases the bulb. The bulb expands by its elastic force and aspirates some blood droplets if the needle is correctly inserted.

What I claim is:

1. An injection syringe device, said device comprising:
    (a) an elongate flexible plastic bag, said bag having at least two opposite side walls, said bag having a first and second ends, with said first end being permanently sealed and said second end being closed by a three layer breakable seal having a foam layer sealed between opposite side walls which breaks automatically when a pre-determined pressure is applied to the exterior of the opposite sidewalls;
    (b) an injection needle mounted on the second end of the bag;
    (c) an elastic plastic bulb inserted between said breakable seal and said injection needle, wherein said plastic bulb may be compressed prior to puncture to enable blood to be withdrawn when said bulb is released.

2. An injection syringe device as claimed in claim 1, wherein said breakable seal comprises a layer of polyethylene ionomer sealed between two layers of polyethylene.

3. An injection syringe device as claimed in claim 1 which further comprises an injectable solution prefilled within said bag.

4. An injectable syringe device as claimed in claim 1 which further comprises an inlet valve which permits the delivery of repetitive injections of solution stored in separate portions of said elongate bag, said portions being separated by a plurality of breakable seals.

5. An injection syringe device, said device comprising:
    (a) a partially flexible plastic bag, said bag having two rigid opposite side walls, joined together by flexible walls, said bag having first and second ends, said first end being permanently sealed,
    (b) a pressure release means closing the second end of said bag, said means consisting of a three layer breakable seal having a foam layer sealed between two bag walls;
    (c) an injection needle sealed on the second end of said bag;
    (d) an elastic plastic bulb inserted between the plastic bag and the injection needle, said bulb providing a means for withdrawing blood by compressing the bulb at the time of puncture.

6. An injection syringe device according to claim 1, characterized in that an injectable solution is prefilled therein and subsequently sterilized.

7. An injection syringe device according to claim 1, which further comprises an inlet valve which permits the delivery of repetitive injections of solutions stored in separate portions of said bag, said portions separated by a plurality of pressure release means.

8. An injection syringe device according to claim 5 which further includes a needle holder formed on the second end of said bag to receive said injection needle.

9. An injection syringe device according to claim 1 wherein the pressure release means consists of a layer of polyethylene ionomer sealed between two layers of polyethylene.

10. An injection syringe device, said device comprising:
    (a) an elongate flexible plastic bag, said bag having at least two opposing side walls, a first end and a second end, said first end may be permanently sealed;
    (b) an injection needle mounted on the second end of the bag;
    (c) a three layer breakable seal closing the second end of the bag adjacent said injection needle, said seal adapted to break when a predetermined pressure is applied to the opposing side walls of the bag.

11. An injection syringe device as claimed in claim 10 wherein the opposing side walls are rigid cover foils and the three layer breakable seal consist of a breakable foam layer sealed between the rigid cover foils.

12. An injection syringe device as claimed in claim 10 wherein the opposing side walls are foils of polyethylene and the three layer breakable seal consists of a layer of polyethylene inomer sealed between two foils of polyethylene.

13. An injection syringe device as claimed in claim 10 or 11 or 12 wherein an elastic plastic bulb is inserted between the plastic bag and the hollow injection needle, whereby said bulb may be compressed prior to puncture to withdraw droplets of blood as the bulb is released, to thereby assist in the identification of venous or arterial penetration.

14. An injection syringe device as claimed in claim 10 or 11 or 12 which further comprises an inlet and outlet valve permitting the delivery of repetitive injections of solutions stored in separate portions of said bag.

15. An injection syringe device as claimed in claim 14 which further comprises an inlet and outlet valve permitting the delivery of repetitive injections of solutions stored in separate portions of said bag.

16. An injection syringe device as claimed in claim 10 or 11 or 12 wherein the device is prefilled with an injectable solution before said first end is sealed.

17. An injection syringe device as claimed in claims 1, 5, or 11 wherein the foam layer is selected from the group of foamed polyethylene, polypropylene, copolymers of polyethylene and vinyl acetate or ethyl acrylate, polyanide, polyvinyl chloride or polystyrene.

18. An injection syringe device as claimed in claim 10 or 11 or 12 wherein the device is prefilled with injectable solution and subsequently sterilized.

* * * * *